(12) United States Patent
Echegaray et al.

(10) Patent No.: US 6,469,163 B1
(45) Date of Patent: Oct. 22, 2002

(54) METHOD FOR PRODUCTION OF HYDROXYLAMINE SULFATE IN THE CONVENTIONAL PROCESS FOR THE SYNTHESIS OF CAPROLACTAM

(75) Inventors: Diego Fernandez Echegaray; Antonio Augusto M. Velloso, both of Salvador (BR); Matthew Lincoln Wagner, White Plains, NY (US)

(73) Assignee: Praxair Technology Inc., Danbury, CT (US)

( * ) Notice: Subject to any disclaimer, the term of this patent is extended or adjusted under 35 U.S.C. 154(b) by 0 days.

(21) Appl. No.: 09/221,209

(22) Filed: Dec. 24, 1998

(51) Int. Cl.$^7$ ............................................. C07D 201/04
(52) U.S. Cl. ....................... 540/535; 423/400; 423/405; 540/536
(58) Field of Search ................................ 423/392, 393, 423/400, 405; 540/535, 536

(56) References Cited

U.S. PATENT DOCUMENTS

| | | | |
|---|---|---|---|
| 3,720,755 A | 3/1973 | Duyverman et al. | ......... 423/307 |
| 4,183,906 A | 1/1980 | Watson et al. | ............... 423/392 |
| 4,235,858 A | 11/1980 | Blakey et al. | ............... 423/393 |
| 5,777,163 A | 7/1998 | Müller et al. | ................. 564/301 |
| 5,985,230 A | * 11/1999 | Vlaming et al. | ............. 423/392 |

FOREIGN PATENT DOCUMENTS

| | | |
|---|---|---|
| EP | 0194715 | 9/1986 |
| EP | 0799794 A1 | 10/1997 |
| FR | 1539288 | 8/1968 |
| GB | 803211 | * 10/1958 .................. 423/392 |

OTHER PUBLICATIONS

A.H. de Rooij et al., "Caprolactime le Procédé HPO", Informantions Chimie no 165–Avril 1977–121. (No month).
E. Faried et al., "Boosting Existing Nitric Acid Production", The Fertiliser Society of London –Oct. 16, 1986.
A.H. de Rooij et al., "XP–002133389 Caprolactam, the HPO process", Chemical Abstracts, vol. 87 1977 No. 2, (No month).

* cited by examiner

Primary Examiner—Wayne Langel
(74) Attorney, Agent, or Firm—Bernard Lau

(57) ABSTRACT

An improvement in the conventional process for the production of caprolactam. The process involves:

(a) reacting air with ammonia gas in an ammonia conversion zone to produce nitric oxide;

(b) oxidizing a portion of the nitric oxide to nitrogen dioxide to produce an $NO_x$-rich process gas stream;

(c) reacting the $NO_x$-rich stream with ammonium carbonate in a nitriting zone to produce ammonium nitrite;

(d) reducing the ammonium nitrite to hydroxylamine diammonium sulfate;

(e) hydrolyzing the hydroxylamine diammonium sulfate to hydroxylamine sulfate;

(f) oximating the hydroxylamine sulfate with cyclohexanone to produce cyclohexanone oxime; and (g) converting the cyclohexanone oxime to caprolactam.

The process is improved by adding supplemental oxygen downstream of the ammonia conversion zone to increase the quantity and rate of formation of nitrogen dioxide in the $NO_x$-rich process gas stream.

7 Claims, 2 Drawing Sheets

METHOD FOR PRODUCTION OF HYDROXYLAMINE SULFATE IN THE CONVENTIONAL PROCESS FOR THE SYNTHESIS OF CAPROLACTAM

BACKGROUND OF THE INVENTION

Caprolactam can be produced from three hydrocarbon feedstocks: cyclohexane, phenol, and toluene. Approximately 68% of the world's caprolactam capacity is produced from cyclohexane, 31% from phenol, and 1% from toluene. All of the cyclohexane and phenol-based production proceeds via the formation of cyclohexanone oxime. In 94% of the cyclohexane-based and phenol-based caprolactam capacity, the formation of this oxime requires an ammonia oxidation step.

In the processes involving ammonia oxidation, caprolactam production from cyclohexane or phenol can be broken down into the following steps:

Oxidation of cyclohexane or hydrogenation of phenol, to synthesize cyclohexanone;

Oxidation of ammonia to form nitric oxide, followed by various reaction steps to form a hydroxylamine salt;

Synthesis of cyclohexanone oxime by reaction of cyclohexanone and the hydroxylamine salt; and Treatment of the cyclohexanone oxime with sulfuric acid followed by neutralization with aqueous ammonia to form caprolactam.

One such method for producing caprolactam is frequently referred to as the "conventional" or "Allied Signal" process. Such process is disclosed, for example, in Weissermel and Arp, Industrial Organic Chemistry (VCH Verlagsgesellschaft mbH 1993), pp. 249–258. In the conventional process, hydroxylamine sulfate $((NH_2OH)_2 \cdot H_2SO_4)$ and aqueous ammonia are reacted to synthesize the oxime. The hydroxylamine sulfate is produced by the Raschig process:

Catalytic air oxidation of ammonia to form nitric oxide:

$$4NH_3 + 5O_2 \rightarrow 4NO + 6H_2O \quad \text{(I)}$$

Continued oxidation of nitric oxide to form nitrogen dioxide:

$$NO + \tfrac{1}{2}O_2 \rightarrow NO_2 \quad \text{(II)}$$

Synthesis of ammonium nitrite:

$$NO + NO_2 + (NH_4)_2CO_3 \rightarrow 2NH_4NO_2 + CO_2 \quad \text{(III)}$$

Reduction of ammonium nitrite to hydroxylamine diammonium sulfate:

$$2NH_4NO_2 + 4SO_2 + 2NH_3 + 2H_2O \rightarrow 2HON(SO_3NH_4)_2 \quad \text{(IV)}$$

Hydrolysis of hydroxylamine diammonium sulfate to hydroxylamine sulfate:

$$2HON(SO_3NH_4)_2 + 4H_2O \rightarrow (NH_2OH)_2 \cdot H_2SO_4 + 2(NH_4)_2SO_4 + H_2SO_4 \quad \text{(V)}$$

Oximating the cyclohexanone with the hydroxylamine sulfate to produce cyclohexanone oxime:

$$C_6H_{10}O + (NH_2OH)_2 \cdot H_2SO_4 + NH_4OH \rightarrow C_6H_{11}NO + (NH_4)_2SO_4 + H_2O \quad \text{(VI)}$$

The process for forming hydroxylamine sulfate in the conventional process is shown in the flow sheet depicted in FIG. 1 of the attached drawing. As shown therein, an air stream 3 is initially compressed in a compressor 10, introduced as a "primary" air stream through feed line 12 into admixture with a gaseous ammonia stream 1, and thereafter fed to a catalytic ammonia converter 20. Typically, 100% ammonia conversion and 95% selectivity to NO are achieved in that reaction. Upon exiting the converter, some of the NO is further oxidized to $NO_2$ to form an $NO_x$-rich process gas stream 2. The water formed in the ammonia oxidation is thereafter removed from the process stream in a condenser 30. Some of the $NO_2$ is absorbed in the water as it is condensed, producing a weak nitric acid condensate 5.

The $NO_x$-rich process gas stream 7 exiting the condenser 30 is then contacted countercurrently with an aqueous ammonium carbonate stream 9 in a trayed absorption tower 40, referred to as a "nitrite tower". In the conventional process additional, "secondary" air is added either directly into the nitrite tower through line 11 or into the $NO_x$ process stream through line 13. The amount of secondary air fed to the nitrite tower affects the relative concentrations of NO and $NO_2$ in the tower. An ammonia stream 15a may also be added to the tower to recover $CO_2$.

Ammonium nitrite is desirably formed in the nitrite tower, according to the reaction:

$$NO + NO_2 + (NH_4)_2CO_3 \rightarrow 2NH_4NO_2 + CO_2 \quad \text{(VII)}$$

The $CO_2$ liberated in this reaction can be recovered in-situ as ammonium carbonate by reaction with the ammonia stream 15, according to the reaction:

$$CO_2 + 2NH_3 + H_2O \rightarrow (NH_4)_2CO_3 \quad \text{(VIII)}$$

An undesired product, ammonium nitrate, is also formed in the nitrite tower by the following reactions:

$$2NO_2 + H_2O \rightarrow HNO_3 + HNO_2 \quad \text{(IX)}$$

$$HNO_3 + HNO_2 + 2NH_3 \rightarrow NH_4NO_2 + NH_4NO_3 \quad \text{(X)}$$

Ammonia participating in reaction (X) may be derived from the dissociation of the ammonium compounds formed in these reactions.

The nitrite tower 40 must be operated to minimize the formation of nitrate. To accomplish this, an approximate 1:1 molar ratio of NO to $NO_2$ should be maintained in the tower. In order to maintain such ratio, secondary air is added to the nitrite tower in the conventional process in amounts of about 5 to 10 volume % of the total air flow into the system.

The vent gas 17 exiting the nitriting tower must be properly regulated to minimize the emission of $NO_x$. An increase in production of hydroxylamine sulfate typically results in a corresponding increase in $NO_x$ emission in the vent gas 17.

The nitrite-rich aqueous solution 19 is then reacted with a sulfur dioxide stream 21 and an ammonia stream 15b fed into a disulfonate column 50 to form hydroxylamine diammonium sulfate. In some systems the ammonia may rather be admixed with the nitrite-rich aqueous solution 19 from the nitrite tower and the mixture then introduced into the disulfonate column.

The hydroxylamine diammonium sulfate stream 23 removed from the disulfonate column is conventionally hydrolyzed in a hydrolysis column 60 to form hydroxylamine sulfate. A portion of the hydroxylamine diammonium sulfate is recycled through line 27 to the disulfonate column 50. The hydroxylamine sulfate solution exiting the hydrolysis column is then recovered from line 25 for use in the oximation process.

In view of the strict environmental regulation of $NO_x$ emissions, the quantity of $NO_x$ gases vented through line 17 cannot be increased. Accordingly, any increased hydroxylammonium sulfate production (and subsequent caprolactam production) must be obtained without any increase in $NO_x$ emissions. This can be accomplished by increasing the amount of air and ammonia fed to the process while increasing the plant size, e.g., the size of the nitrite tower 40 and air compressor 10. However, such an increase in equipment capacity requires substantial capital investment.

There is therefore a need for the development of improved techniques in the conventional process for producing caprolactam, by which increased amounts of hydroxylamine sulfate and, consequently, caprolactam can be produced without large capital investment, and without increasing $NO_x$ emissions.

SUMMARY OF THE INVENTION

The present invention provides just such an improvement in the conventional process for the production of caprolactam involving:

(a) reacting air with ammonia gas in an ammonia conversion zone to produce nitric oxide;

(b) oxidizing a portion of the nitric oxide to nitrogen dioxide to produce an $NO_x$-rich process gas stream;

(c) reacting the $NO_x$-rich stream with ammonium carbonate in a nitriting zone to produce ammonium nitrite;

(d) reducing the ammonium nitrite to hydroxylamine diammonium sulfate;

(e) hydrolyzing the hydroxylamine diammonium sulfate to hydroxylamine sulfate;

(f) oximating the hydroxylamine sulfate with cyclohexanone to produce cyclohexanone oxime; and (g) converting the cyclohexanone oxime to caprolactam.

In accordance with the invention, the foregoing process is improved by adding supplemental oxygen downstream of the ammonia conversion zone to increase the quantity and rate of formation of nitrogen dioxide in the $NO_x$-rich process gas stream. Desirably, secondary air, normally introduced into the nitriting zone (or into the $NO_x$-rich gaseous stream feeding into the nitriting zone) is rerouted to the ammonia conversion zone to increase the production of nitric oxide formed in the ammonia conversion zone without increasing the level of $NO_x$ contained in the gas vented from the nitriting zone.

Utilizing the improved technique of the invention, desirably by rerouting the secondary air to the ammonia conversion zone and maintaining the volumetric percentage of ammonia fed to the conversion zone at a constant or increased level, the production of NO in the conversion zone is increased. By adding supplemental oxygen according to the invention, both the amount and rate of conversion of NO to $NO_2$ are increased, thereby promoting formation of nitrite in the nitriting zone, without any adverse effect on the $NO_x$ content of gases vented from the nitriting zone. Alternatively, the addition of supplemental oxygen may be used to lower $NO_x$ emissions, with or without rerouting of secondary air to the ammonia conversion zone, and with or without increases in nitrite (and consequently hydroxylamine sulfate and caprolactam) production. The invention also encompasses adding supplemental oxygen according to the invention without rerouting secondary air to the ammonia converter, but increasing the volumetric percentage of ammonia fed to the conversion zone to increase production of NO. This ultimately results in an increase in formation of hydroxylamine sulfate and caprolactam without an increase in $NO_x$ emissions.

The method of the present invention thus facilitates an increase in hydroxylamine sulfate production in the conventional process for synthesizing caprolactam, while maintaining $NO_x$ emissions at constant, or decreased, levels. It is estimated that use of the method of the invention normally results in an increase of between about 5 and 15% in the production of hydroxylamine sulfate without increasing $NO_x$ emissions. Furthermore, this is accomplished without substantial capital investment, such as would otherwise be required to increase plant capacity. Moreover, by substituting oxygen for inert nitrogen present in the secondary air conventionally fed to the nitriting zone, the oxygen partial pressure in the system may be increased and residence times for the intermediates formed in the various stages of the process may be lowered.

In the production of nitric acid, it is known that direct injection of supplemental oxygen can boost nitric acid synthesis while controlling $NO_x$ emissions. Such addition of oxygen is described, for example, in U.S. Pat. Nos. 4,183,906; 4,183,906; 4,235,858; and 5,167,935; UK Patent No. 803211; and EP published Patent Applications Nos. 799794 and 808797. Oxygen addition is also described in Kongshaug, Extension of Nitric Acid Plant Capacity by Use of Oxygen, Nitric Acid Symposium (1981); and by Faried et al., Boosting Existing Nitric Acid Production, The Fertiliser Society (1986). For example, EP 808797 describes an improved process for nitric acid production in which supplemental oxygen is added to the cooler/condenser, the absorption tower, the ammonia converter, and/or the bleacher, to cause an increase in nitric acid production without increasing $NO_x$ emissions. No supplemental oxygen addition of this type is believed to have been previously disclosed in connection with the synthesis of caprolactam.

Feeding oxygen to the ammonia converter has been employed in the BASF and Inventa processes for the synthesis of caprolactam. (As described, for example, in the Kirk Othmer Encyclopedia of Chemical Technology, $4^{th}$ edition, 4:831 (1992) and U.S. Pat. No. 5,777,163.) In these processes, however, no supplemental oxygen is added downstream of the converter. Also, the BASF and Inventa processes differ substantially from the conventional process for producing caprolactam in that they do not add air to the ammonia converter, and do not involve the formation of $NO_2$.

DETAILED DESCRIPTION OF THE INVENTION

All patent applications, patents, and literature references cited in this specification are hereby incorporated by reference in their entirety.

In accordance with the present invention, a supplemental oxygen stream 8, (see FIG. 2) is injected downstream of the ammonia converter 20 of the hydroxylamine sulfate reaction train (FIG. 1) in the conventional process for the synthesis of caprolactam. As used herein, the term "supplemental oxygen" refers to pure oxygen or any oxygen-enriched gaseous stream containing more than about 50%, and preferably more than about 90%, oxygen by volume. Suitable supplemental oxygen sources include pipeline oxygen, independent cryogenic oxygen plants or PSA/VPSA oxygen plants, liquid oxygen tanks or oxygen-enriched air streams.

Figure 1:
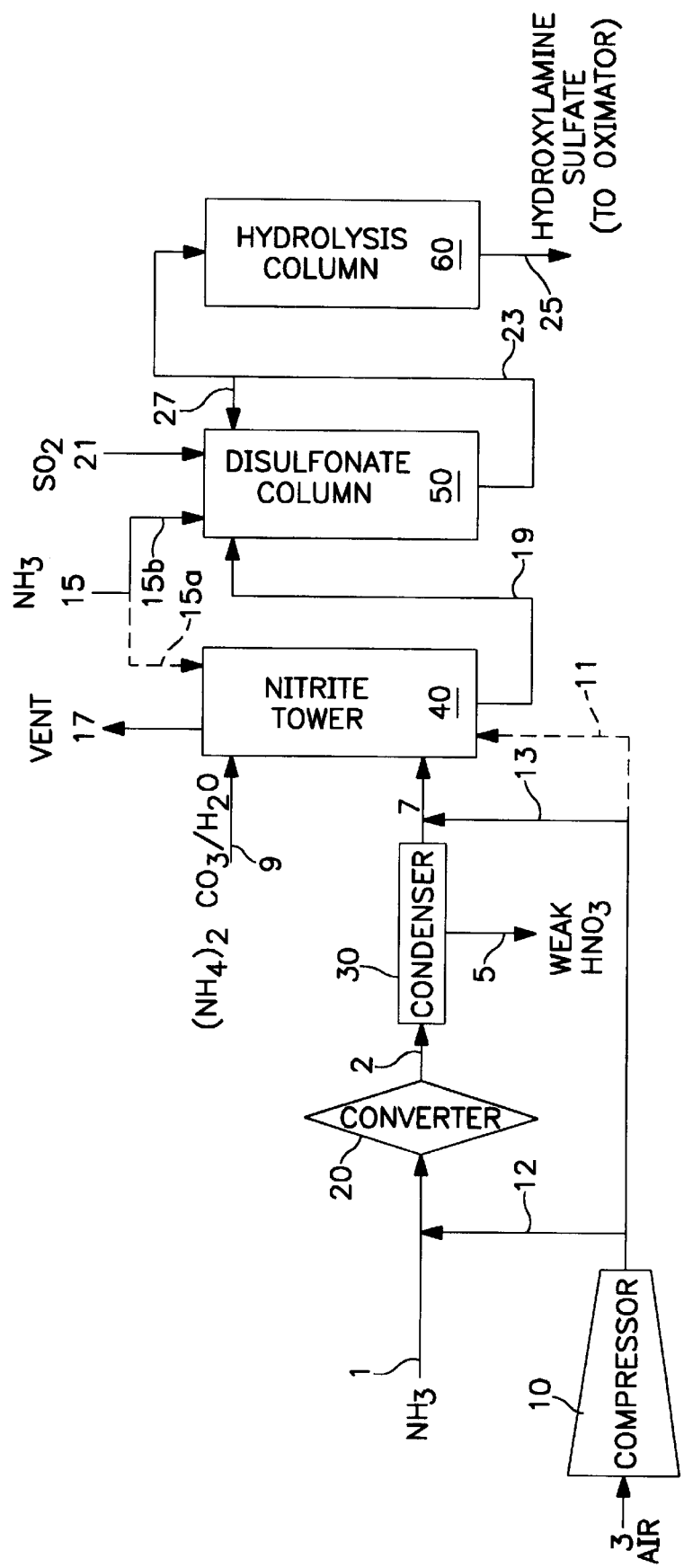
FIG. 1 is a schematic flow sheet of the hydroxylamine sulfate section of the prior art conventional process for the production of caprolactam.

The supplemental oxygen is injected in place of the secondary air introduced to the nitrite tower in the conventional process through lines 11 or 13 (FIG. 1). In accordance with a preferred embodiment of the present invention, air that would otherwise have been employed as "secondary" air is instead fed through feed line 12 for introduction as primary air into the ammonia converter 20. Gaseous mixtures containing about 8 to 12 mole % ammonia and about 18 to 20 mole % oxygen are thus introduced into the ammonia converter, and converted therein under the reaction conditions, e.g., temperature, pressure and catalyst, utilized in the conventional process to produce gaseous reaction mixtures containing in mole %, about:

7 to 12% NO 11 to 18% $H_2O$ 67 to 72% $N_2$ 3 to 10% $O_2$

By thus increasing the flow of primary air introduced into the ammonia converter, the amount of NO formed therein is increased by about 5 to 15% as compared with ammonia oxidation step in the absence of the addition of supplemental oxygen according to the invention.

The supplemental oxygen is admixed with the $NO_x$-rich process gas stream 7 introduced to the nitrite tower 40 in the proportion of about 1 to 2 moles of $O_2$ per mole of incremental NO produced in the ammonia converter (i.e., per mole of additional NO produced as a result of introducing additional primary air and ammonia according to the preferred embodiment of the invention). By thus increasing the amount of oxygen introduced into the nitriting zone, both the quantity and rate of formation of $NO_2$ and ammonium nitrite are enhanced, without adversely affecting the desired $NO:NO_2$ ratio in the reaction mixture.

Figure 2:
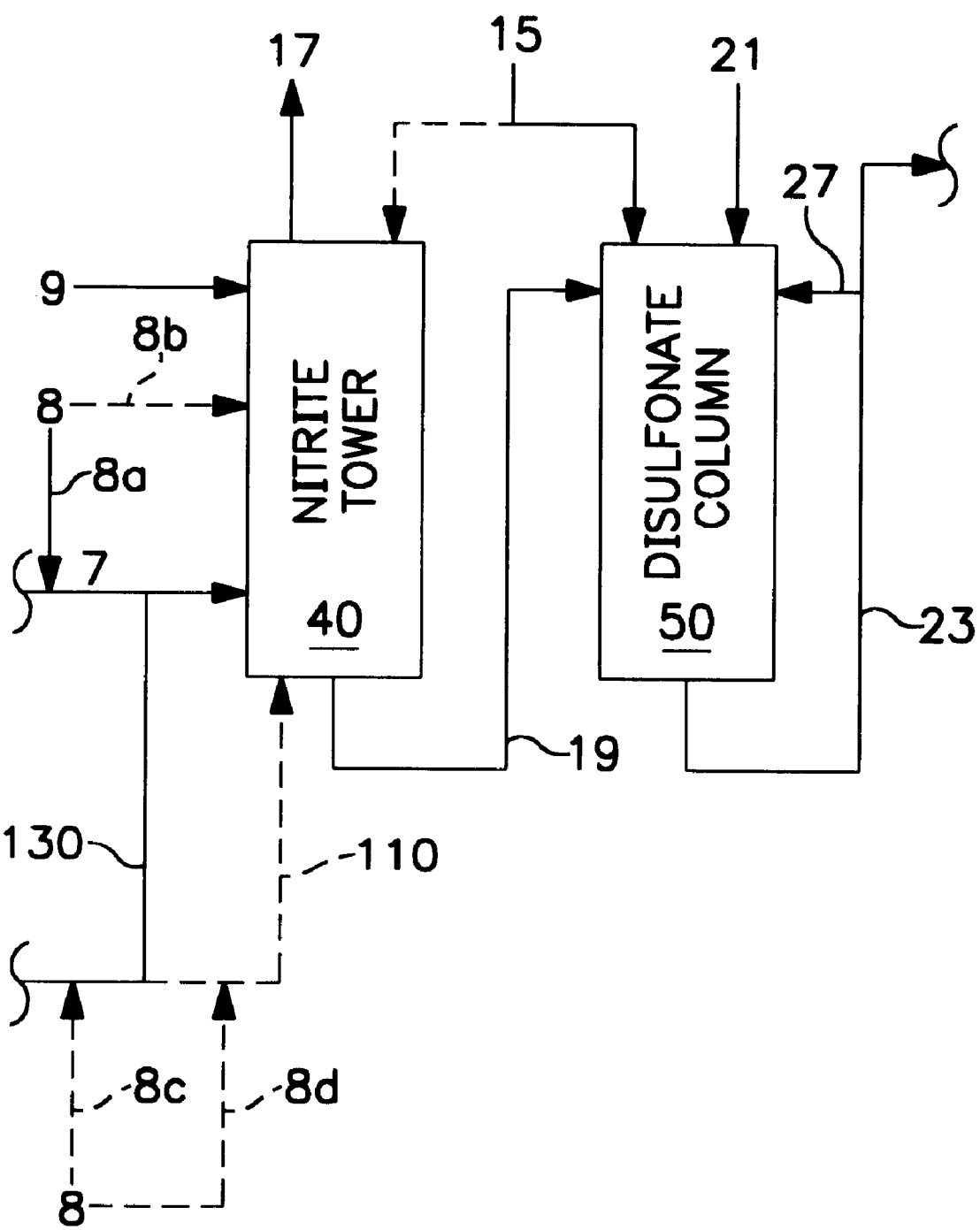
FIG. 2 is a schematic flow sheet of a portion of the conventional process reaction train as modified in accordance with the present invention.

The supplemental oxygen may be added to the nitriting zone through any of the alternative streams shown in FIG. 2. For example, in one embodiment of the invention the supplemental oxygen stream 8 is injected via line 8a into the process gas line 15 entering the nitrite tower 40. Alternatively, the supplemental oxygen 8 may be injected through line 8b directly into the nitrite tower 40. It is also feasible to inject the supplemental oxygen 8 via lines 8c and 13 into process gas line 7, or via lines 8d and 11 directly into the nitrite tower. The invention also encompasses the direct addition of the supplemental oxygen at several locations in the nitrite tower. If injected at a single location, however, it is preferable to add the supplemental oxygen 8 via lines 8c and 13, or 8d and 11, as indicated above. The supplemental oxygen is preferably introduced into the nitrite tower under positive pressures of between about 2 and 20 psig, typically about 5 psig.

As noted above, practice of the improved method of this invention does not involve any capital investment of the order of that which would be required to, e.g., expand the capacity of the nitriting unit. Furthermore, retrofitting of existing plants to practice the improved technique of the invention can be easily carried out by providing the necessary supplemental oxygen supply lines and connecting them by conventional means to the relevant process line or process unit as outlined above.

It is estimated that roughly 2.8 tons of oxygen may typically be consumed in the method of the invention for every additional ton of ammonia added to the ammonia converter, although the invention may be practiced using lower and higher amounts of oxygen consumption.

While preferred embodiments of the process hereof are described hereinabove, it will be apparent to those skilled in the art that various changes may be made therein without departing from the scope of the invention as defined in the claims appended hereto.

We claim:

1. In a process for the production of caprolactam, which comprises:
   (a) reacting air with ammonia gas in an ammonia conversion zone to produce nitric oxide;
   (b) oxidizing a portion of the nitric oxide to nitrogen dioxide to thereby produce an $NO_x$-rich process gas stream;
   (c) reacting the $NO_x$-rich stream with ammonium carbonate in a nitriting zone to produce ammonium nitrite;
   (d) reducing the ammonium nitrite to hydroxylamine diammonium sulfate;
   (e) hydrolyzing the hydroxylamine diammonium sulfate to hydroxylamine sulfate;
   (f) oximating the hydroxylamine sulfate with cyclohexanone to produce cyclohexanone oxime; and
   (g) converting the cyclohexanone oxime to caprolactam;
   the improvement comprising adding supplemental oxygen downstream of the ammonia conversion zone while simultaneously rerouting secondary air to the ammonia conversion zone to increase the production of nitric oxide formed in the ammonia conversion zone and the quantity and rate of formation of nitrogen dioxide in the nitriting zone, while maintaining a substantially equimolar $NO:NO_2$ ratio in the $NO_x$-rich stream in the nitriting zone.

2. The process of claim 1 further comprising rerouting secondary air from the nitriting zone to the ammonia conversion zone.

3. The process of claim 1 wherein the supplemental oxygen is added into a secondary air stream providing air to the nitriting zone.

4. The process of claim 1 wherein the supplemental oxygen is added into a secondary air stream providing air to the $NO_x$-rich process gas stream upstream of the nitriting zone.

5. The process of claim 1 wherein the supplemental oxygen is added directly into the nitriting zone.

6. The process of claim 1 wherein the supplemental oxygen is added to the $NO_x$-rich process gas stream upstream of the nitriting zone.

7. The process of claim 1 wherein the supplemental oxygen is a gas comprising more than about 90 vol. oxygen.

* * * * *